United States Patent [19]

Dellinger et al.

[11] 4,015,333
[45] Apr. 5, 1977

[54] ORTHODONTIC BAND FORMING METHOD AND APPARATUS

[76] Inventors: Eugene L. Dellinger, 1326 Old Lantern Trail, Fort Wayne, Ind. 46825; Robert J. Loubier, 5122 Chippewa Court, Fort Wayne, Ind. 46804

[22] Filed: Oct. 22, 1975

[21] Appl. No.: 624,951

[52] U.S. Cl. .............................................. 32/14 A
[51] Int. Cl.² .......................................... A61C 7/00
[58] Field of Search .......... 29/421 M, 208; 32/14 A

[56] References Cited

UNITED STATES PATENTS

| 3,426,564 | 2/1969 | Jansen et al. | 29/421 M |
|---|---|---|---|
| 3,590,464 | 7/1971 | Wildi | 29/421 M |

Primary Examiner—Robert Peshock
Attorney, Agent, or Firm—Gust, Irish, Jeffers & Rickert

[57] ABSTRACT

Method and apparatus for providing an orthodontic band shaped to an individual tooth is disclosed wherein a tooth replica is encircled by the band and optionally an annular conducting member surrounds the band. The band is shaped to the tooth by rapidly changing a magnetic field within the band and annular member to induce a current flow which cooperates with the magnetic field to force the band radially inwardly into close conformity with the replica. The replica and annular member are then separated from the band and the band is applied to the original tooth.

12 Claims, 6 Drawing Figures

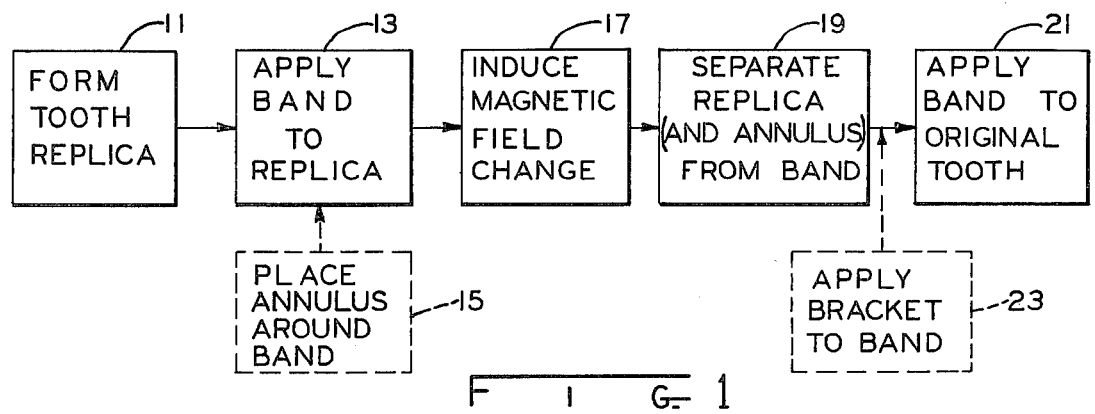
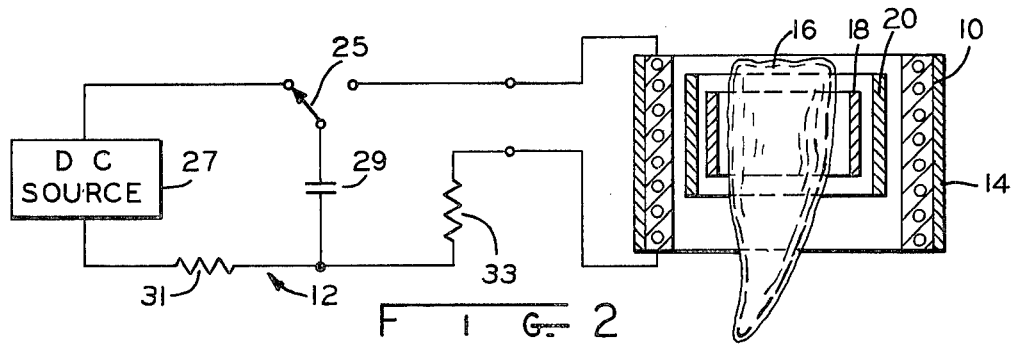
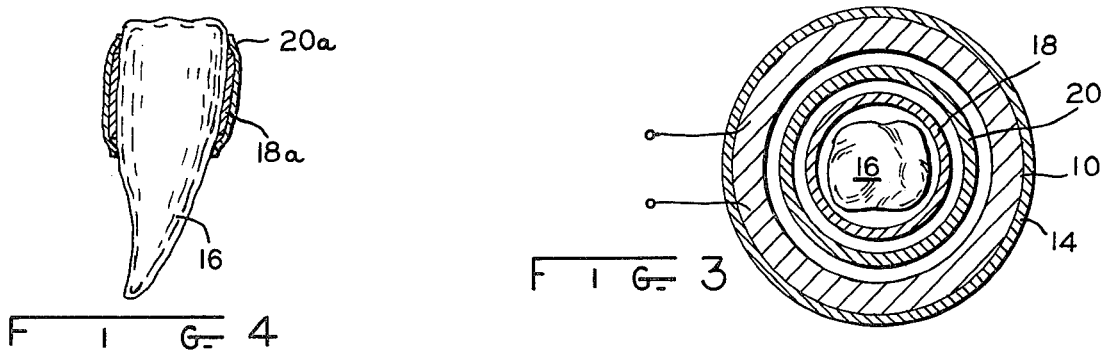
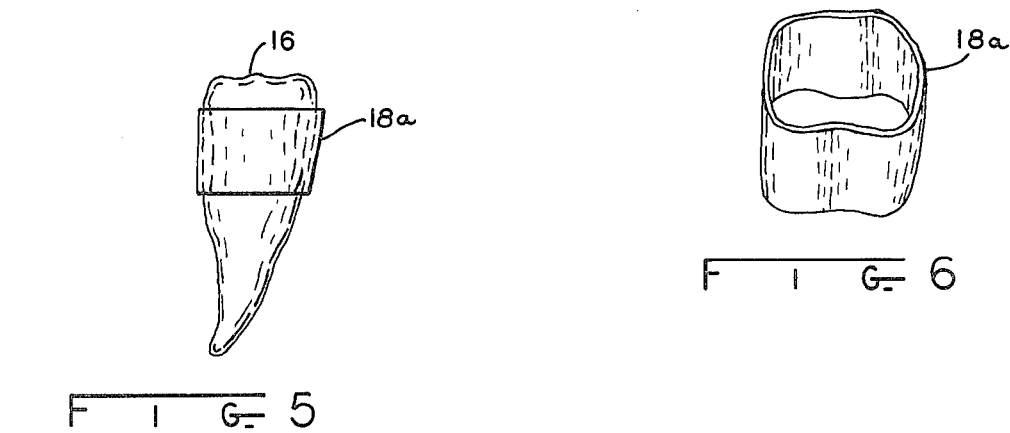

ORTHODONTIC BAND FORMING METHOD AND APPARATUS

BACKGROUND OF THE INVENTION

Field of the Invention

The present invention relates generally to the field of orthodontics and more particularly to a method and apparatus for conforming an orthodontic band to the peripheral contour of an individual tooth.

Orthodontia is a highly developed art with a typical treatment sequence including the forming of an impression of the patient's teeth and then forming a replica of those teeth from the impression. In some treatment procedures the replica of the entire set of teeth may then be separated into individual teeth and those individual teeth rearranged into the preferred or intended resulting configuration. Orthodontic bands of approximately the correct size are formed by hand to the configuration of certain of the teeth, brackets attached to those orthodontic bands and the bands placed in the patient's mouth on those teeth to receive an archwire stressed in a manner to urge the respective teeth toward the preferred arrangement. In such a typical process the forming of blank bands to conform to the desired contour of an individual tooth is a time consuming and expensive hand process.

Similar hand forming of orthodontic bands has been heretofore required in implementing variations on the above general orthodontic procedure such as the "Method and Apparatus for Orthodontic Treatment" disclosed in copending application Ser. No. 561,697 filed Mar. 25, 1975.

SUMMARY OF THE INVENTION

Among the several objects of the present invention may be noted the provision of method and apparatus for reducing the overall cost of orthodontic treatment; the provision of apparatus to crimp or constrict an orthodontic band about a tooth replica or other mandrel; the provision of a process for rapidly conforming an orthodontic band to the peripheral contour of an individual tooth; and the provision of a system for rapidly conforming an orthodontic band to an individual tooth characterized by its efficiency, economy and accuracy of fit.

In general, this invention includes the method of conforming an orthodontic band to the peripheral contour of a tooth which comprises forming a replica of that tooth, applying an orthodontic band to the replica and rapidly changing a magnetic field within the band to induce a current flow around the band which produces a counteracting magnetic field that crimps the band closely about the replica. An annulus of good conducting material may be provided about the band to increase the induced current flow and, after forming, the replica and annulus if present are removed and the band placed over the individual tooth.

Also in general and in one form of the invention, an orthodontic band is conformed to a desired contour by placing the band over a mandrel such as a tooth replica, placing an annulus of good conducting material around the band and rapidly changing the magnetic field within the band and annulus to induce a current around the annulus to interact with the field forcing the band radially inwardly against the mandrel. Thereafter the band is removed from the mandrel and the annulus removed from the band for subsequent utilization of the band.

Further in general and in one form of the invention, apparatus for shaping an orthodontic band to an individual tooth includes a tooth replica, an orthodontic band of suitable size to girdle the replica, an annulus of good conducting material for encircling the band, and means for magnetically forming the band radially inwardly into close conformity with the replica. The means for forming may include a coil for producing a magnetic field through the annulus and means for rapidly changing the coil field thereby inducing a current flow in the annulus to interact with the field and force the band radially inwardly against the replica.

The above-mentioned and other features and objects of this invention and the manner of attaining them will become more apparent and the invention itself will be best understood by reference to the following description taken in conjunction with the accompanying drawings.

BRIEF DESCRIPTION OF THE DRAWINGS

FIG. 1 is a functional block diagram of an overall process according to the present invention;

FIG. 2 is a schematic diagram illustrating apparatus according to the present invention in one form;

FIG. 3 is a top view of the coil, band, annulus and replica of FIG. 2;

FIG. 4 is a view inn cross-section illustrating the replica and the band and annulus as conformed thereto;

FIG. 5 is a plan view of the replica and conformed band; and

FIG. 6 is a perspective view of the completed formed band ready for application to the original tooth.

Corresponding reference characters indicate corresponding parts throughout the drawing and the following examples illustrate the invention in one form thereof and are not to be construed as limiting in any manner.

DESCRIPTION OF THE PREFERRED EMBODIMENT

Referring now to the drawing in greater detail FIG. 1 illustrates a typical sequence of events in carrying out the present invention. A mandrel or form such as a replica of a tooth is first created at 11 by forming an impressionn of a set of teeth, making a working cast of the set of teeth from the impression and sectioning that working cast to separate the replica of the tooth from the working cast. Generally several different tooth replicas will be sectioned out of the working cast. An unformed orthodontic band of suitable size to girdle the replica is placed in position about the replica at 13 and optionally an annulus of good conducting material is placed around the band as illustrated by block 15. This optional annulus is employed when orthodontic bands of poor electrical conductivity such as plastic materials or some stainless steel materials are being used. Orthodontic bands of precious metals such as silver are adequately conductive and the annulus step 15 may be omitted. A change in the magnetic field through the band is then indicated by step 17 which change is sufficiently rapid to induce a current flow about the band, annulus or both which interacts with the field to collapse the band firmly against the replica periphery. At 19 the replica and annulus, if present, are separated from the band, for example, by employing solvents either with or without an accompanying chemical change which effectively dissolves the replica or annulus leaving the band accurately formed for application to the original tooth at 21. An orthodontic bracket may optionally be attached to the band by weld or silver solder as desired which bracket effects the coupling between the band and archwire as known in the art.

In the event that a tooth replica is undercut or has other irregularities which would render the subsequent application of the band to the original tooth difficult, the irregularily may be filled in with, for example, a dental plastic material before forming the orthodontic band thereto. Generally, however, replicas formed by the foregoing techniques do not have problem irregularities.

Considering now FIGS. 2 and 3, a magnetic coil 10 is coupled to a source 12 by a double pole single throw switch 24 which upon actuation provides a pulse of electrical energy to the coil 10. Situated inside the coil 10 is a cast replica 16 of a tooth which is made of a suitable soluble plastic of the acrylic type frequently employed in modern dentistry. Surrounding the replica 16 is a thin walled sleeve 18 of stainless steel consituting the unformed orthodontic band and around this is another sleeve or annular member 20 of highly conductive metal such as copper. Upon application of an electrical pulse to the coil 10 a voltage is induced in the copper sleeve 20 which produces a current flowing in a direction which creates a magnetic field opposed to that of the coil 10. The interaction of the magnetic fields compresses that sleeve 20 radially inardly against the stainless steel band 18 and that band in turn intimately about the tooth replica 16. The resulting configuration of the band 18 is illustrated as 18a in FIGS. 4, 5 and 6 and the resulting configuration of the copper sleeve 20 is illustrated as 20a in FIG. 4.

The radially inwardly directed force against the sleeve 20 and band 18, according to well known physical principles, has an equal and opposite force exerted outwardly on the coil 10 and accordingly this coil 10 should be supported within a relatively sturdy structure 14.

To provide the pulse of electrical energy to magnetically form the sleeve 20 and band 18, a high voltage direct current source 27 may be employed. With the switch 25 in the position shown this direct current source 27 charges a capacitor or bank of capacitors 29 by way of a current limiting resistor 31. Circuit values may be chosen so that this charging time is relatively short as compared to the time required to place a replica and bands within the coil. With the replica and bands positioned within the coil 10 and the capacitor 29 charged the operator then moves the switch 25 so as to discharge capacitor 29 through the coil 10 providing the desired pulse. A current limiting resistor 33 may be provided if the resistance of the coil 10 is not as high as desired however this current limiting resistor 33 generally is not necessary. The parallel combination of capacitor 29 and coil 10 may be overdamped, critically damped, or underdamped as desired so long as a substantial energy pulse is delivered to the coil 10 to rapidly change the magnetic field of that coil.

The formed copper sleeve or annulus 20a may be removed for example by a solution of sulphuric acid which chemically dissolves the copper while not affecting the stainless steel band 18a. The replica 16 may also be dissolved in a suitable solvent which will not attack the stainless steel band 18a. At this point in the process the replica 16 and annular member 20a have performed their intended function and their destruction during removal is immaterial.

From the foregoing it is now apparent that a novel method and apparatus for forming an orthodontic band has been presented meeting the opjects and advantageous features set out hereinbefore as well as others. Numerous modifications will readily suggest themselves to those of ordinary skill in the art. For example the electrical source 12 has been illustrated in a very simple form, however, it is contemplated that more sophisticated capacitor banks, high voltage switching for example employing ignitrons, and triggering circuitry therefor may be employed. These and other variations will readily suggest themselves to those of ordinary skill in the art and accordingly the scope of the present invention is to be measured only by that of the appended claims.

What is claimed is:

1. The method of conforming an orthodontic band to thee peripheral contour of an individual tooth comprising the steps of:
   forming a replica of the tooth;
   applying an orthodontic band to the replica;
   and rapidly changing the magnetic field within the band to induce a current flow around the band which current flow interacts with the magnetic field to crimp the band closely about the replica.

2. The method of claim 1 comprising the further steps of removing the replica from the band and placing the band over the individual tooth.

3. The method of claim 2 wherein the step of removing the replica destroys the replica.

4. The method of claim 1 comprising the further step of providing an annulus of good conducting material around the band to increase the induced current flow and therefore also the crimping force.

5. The method of claim 4 including the additional step of removing the annulus from the band after the band is crimped about the replica.

6. The method of claim 5 wherein the step of removing comprises placing the band and annulus into a solution in which the annulus is soluble and the band is insoluble.

7. The method of claim 4 comprising the further step of removing the replica from the band and placing the band over the individual tooth.

8. The method of claim 7 wherein the step removing the replica destroys the said replica.

9. The method of claim 8 including the additional step of removing the annulus from the band after the band is crimped about the replica.

10. The method of claim 1 wherein the step of forming a replica of the tooth includes the steps of forming an impression of a set of teeth, making a working cast of the set of teeth from the impression, and sectioning the working cast to at least separate the replica of the tooth from the working cast.

11. Apparatus for providing an orthodontic band shaped to an individual tooth comprising:
    a replica of the tooth;
    an orthodontic band of suitable size to girdle the replica,
    an annulus of good conducting material for encircling the band; and
    means for magnetically forming the band radially inwardly into close conformity with the replica.

12. The apparatus of claim 11 wherein the means for forming comprises a coil for producing a magnetic field and means electrically coupled to the coil for rapidly changing the coil field thereby inducing a current flow in the annulus which current interacts with the magnetic field to force the band radially inwardly against the replica.

* * * * *

UNITED STATES PATENT OFFICE
CERTIFICATE OF CORRECTION

Patent No. 4,015,333          Dated April 5, 1977

Inventor(s)  Eugene L. Dellinger, Robert J. Loubier

It is certified that error appears in the above-identified patent and that said Letters Patent are hereby corrected as shown below:

IN THE SPECIFICATION

Column 3, line 29      "inardly" should be --inwardly--
Column 4, line 3       "opjects" should be --objects--

IN THE CLAIMS

Claim 1, Column 4, line 17     "thee" should be --the--

Signed and Sealed this

Fourteenth Day of June 1977

[SEAL]

Attest:

RUTH C. MASON
Attesting Officer

C. MARSHALL DANN
Commissioner of Patents and Trademarks